United States Patent [19]
Gaillard et al.

[11] Patent Number: 6,139,795
[45] Date of Patent: Oct. 31, 2000

[54] USE OF MICROPOROUS POLYOLEFIN FOR ABSORBING SWEAT AND OTHER BODILY EXHALATIONS

[75] Inventors: Claude Gaillard, Jebsheim; Jacques Meyer, Sélestat, both of France

[73] Assignee: Daramic, Inc., North Charleston, S.C.

[21] Appl. No.: 09/155,952

[22] PCT Filed: Apr. 10, 1997

[86] PCT No.: PCT/EP97/01757

§ 371 Date: Dec. 28, 1998

§ 102(e) Date: Dec. 28, 1998

[87] PCT Pub. No.: WO97/38736

PCT Pub. Date: Oct. 23, 1997

[30] Foreign Application Priority Data

Apr. 12, 1996 [DE] Germany .......................... 196 16 224

[51] Int. Cl.$^7$ .......................... A61L 9/012; A43B 13/38; A01N 25/34
[52] U.S. Cl. .................................... 422/5; 36/43; 424/404
[58] Field of Search .................... 422/5; 36/43; 424/402, 424/404, 411

[56] References Cited

U.S. PATENT DOCUMENTS

| | | |
|---|---|---|
| 4,580,356 | 4/1986 | David . |
| 5,035,886 | 7/1991 | Chakrabarti et al. . |
| 5,216,825 | 6/1993 | Brum . |
| 5,399,404 | 3/1995 | Laughlin et al. . |

FOREIGN PATENT DOCUMENTS

| | | |
|---|---|---|
| 33 06 843 | 9/1983 | Germany . |
| 230 419 | 12/1985 | Germany . |
| 88/03765 | 6/1988 | WIPO . |

*Primary Examiner*—Elizabeth McKane
*Attorney, Agent, or Firm*—Nields & Lemack

[57] ABSTRACT

We describe the use a material which is based on microporous, filler-containing polyolefin and essentially consists of a homogeneous mixture of ultra-high molecular weight polyolefin, filler and plasticizer, for absorbing sweat and other bodily exhalations. This material is preferably treated with antibacterial and/or fungicidal agents and is suitable for avoiding the formation of odor, for example in shoes and articles of clothing. The use in the form of an inner sole which has ribs running at right angles to the longitudinal axis of the inner sole to form hollow spaces is preferred.

15 Claims, No Drawings

USE OF MICROPOROUS POLYOLEFIN FOR ABSORBING SWEAT AND OTHER BODILY EXHALATIONS

The invention relates to the use of a material based on microporous, filler-containing polyolefin for absorbing sweat and other bodily exhalations and for avoiding formation of odour.

Living beings, in particular humans, excrete sweat and other bodily exhalations which lead to an unpleasant formation of odour. A typical example of this are the known sweating feet which lead to an unpleasant formation of odour in footwear. Similar problems exist in other areas of the body and the clothing which covers these areas of the body.

In the past, there has accordingly been no lack of proposals for materials which are said to lead to avoidance or reduction of body odours. Thus, for example, WO 88/03765 discloses a perspiration insert for articles of underwear or clothing which has a skin-friendly absorbent layer of a paper nonwoven, fibre nonwoven, felt, cellulose, cellulose nonwoven or a woven fabric of wool or cotton and a thin outer layer which is impermeable to water, the absorbent layer comprising microencapsulated fragrances and/or microencapsulated active compounds which destroy sweat and/or inhibit the formation of sweat. DD-PS 230 419 furthermore discloses an inner sole of a composite of an extruded polyolefin foam with a textile and with an antimycotic and/or odour-improving treatment, which has, on one or both sides, a compact flexible barrier layer with particular physical parameters of a thermoset, thermoplastic, lefa or of compacted polyolefin foam, which is bonded or glued thermally with the polyolefin foam. DE-A-33 06 843 furthermore discloses absorbent products with an integrated arrangement of a backing layer which is impenetrable to liquid, an absorbent medium on this, and a layer which is penetrable to liquid and lies on the absorbent layer. The backing layer comprises a porous film which is penetrable to vapour and impenetrable to liquid and is produced by mixing 100 parts by weight of a polyolefin resin, 28 to 200 parts by weight of filler particles and 10 to 70 parts by weight of a liquid or wax-like hydrocarbon polymer or a liquid rubber and shaping the mixture to a film. This is then subsequently stretched by 1.2 times the original dimension in at least one surface direction to form fine pores in the film. This absorbent product is preferably a disposable nappy or a sanitary towel.

In contrast, it has now been found, surprisingly, that a material which has already been used for decades as a battery separator in accumulators and batteries is excellently suitable for combating unpleasant odours which are formed by sweat and other bodily exhalations.

The invention accordingly relates to the use of a material which is based on microporous, filler-containing polyolefin and essentially consists of a homogeneous mixture of 8 to 100 vol. % polyolefin having a molecular weight (weight-average) of at least 300,000, a standard load melt index of substantially 0 and a reduced viscosity of not less than 4.0, 1 to 92 vol. % filler and 1 to 40 vol. % plasticizer, for absorbing sweat and other bodily exhalations.

The invention furthermore relates to shoes, articles of clothing, underlays, linings, inserts and parts thereof which comprise the abovementioned material based on microporous, filler-containing polyolefin or consists of this.

Preferred embodiments and advantages of the invention can be seen from the following description and the subclaims.

Although the material used according to the invention is obviously suitable for a large number of uses and can be adapted to these uses in its construction, the main field of use is currently in the shoe sector, in particular as soles or inner soles. The invention is therefore explained below chiefly with the aid of this preferred embodiment, without this being interpreted as a limitation.

As already mentioned above, the material used according to the invention which is based on microporous, filler-containing polyolefin has already been known as a battery separator material for a long time and is described in detail in U.S. Pat. No. 3,351,495 and the corresponding DE-AS 1 496 123. The disclosure of these publications is herewith expressly referred to. The polyolefin is an ultra-high molecular weight polyolefin, preferably ultra-high molecular weight polyethylene. It has an average weight-average molecular weight of at least 300,000, preferably at least 1,000,000, and in particular about 4 to $7 \times 10^6$. The standard load melt index of the polyolefin is substantially 0, i.e. it is less than 0.1, and preferably less than 0.01. The reduced viscosity of the polyolefin is not less than 4.0, and is preferably more than 10, and in particular more than 15. The abovementioned U.S. Pat. No. 3,351,495 and DE-AS 1 496 123 are referred to in respect of the determination of the standard load melt index and reduced viscosity. As explained in these publications, polyolefin mixtures can also be used. In addition to polyethylene, in particular polypropylene, polybutene, polystyrene, ethylene/propylene copolymers, ethylene/hexylene copolymers, ethylene/butene copolymers, propylene/butene copolymers, ethylene/propylene/butene copolymers and copolymers of ethylene or propylene with an ethylenically unsaturated monocarboxylic acid, that is to say acrylic acid, methacrylic acid or mixtures thereof, are also suitable.

Suitable fillers and plasticizers are known to the expert. In this context, reference is again made to U.S. Pat. No. 3,351,495 and DE-AS 1 496 123. A preferred filler is finely divided silica (silicic acid). The average particle size (diameter) of the filler is the range from 0.01 to about 20 $\mu$m, the surface area of the filler being in the range from 30 to 950 $m^2/g$, and preferably at least 100 $m^2/g$.

The material to be used according to the invention comprises a water-insoluble oil, in particular process oil, as a plasticizer.

Preferred ranges of amounts for the homogeneous mixture are 15 to 60 vol. % polyolefin, in particular 30 to 45 vol. % polyolefin, 35 to 80 vol. % filler, in particular 50 to 65 vol. % filler, and 1 to 10 vol. % plasticizer.

In addition to the constituents mentioned, the material to be used according to the invention can comprise customary additives, such as antioxidants (usually 0.1 to 1%), lubricants (usually 0.1 to 1%), antistatics, pigments, dyestuffs, conductive carbon black, stabilizers, light stabilizers and the like.

In a particularly preferred embodiment, the material to be used according to the invention is treated with antibacterial and/or fungicidal agents. These can be applied in any desired form. It is preferable to spray on or coat on these agents in the form of an aqueous solution. The particular amount to be applied depends on the use of the material to be used according to the invention, and is usually 1 to 10 $g/m^2$ of surface area, preferably about 5 $g/m^2$ of surface area. The co-use of surfactants has proved advantageous here. These promote wetting and therefore uniform distribution over the surface and contribute considerably towards the absorbency of the material and therefore to effective combating of odours. Surfactants having the formula R—O—$R_1$, in which R is a branched or straight-chain, substituted or unsubstituted alkyl, alkenyl or alkinyl radical having 6 to 50 carbons atoms and $R_1$ is an oxyalkyl, glyceroloxyalkyl or sorbitanoxyalkyl radical, the degree of oxalkylation being 2 to 80, are particularly suitable. An example which is particularly suitable according to the invention is the surfactant with the formula R—O—$(C_2H_4O)_x$—$(C_3H_6O)_y$—H, wherein R is a $C_{12}H_{25}$ to $C_{18}H_{37}$ radical, x is 8 and y is 6 to 10. Such surfactants are commercially obtainable under the name PLURAFAC® LF 700 from BASF.

When used in the shoe sector in particular, a composition which comprises 25 to 35 wt. % of a solution of the abovementioned surfactant in aqueous isopropyl alcohol (28 wt. % surfactant, 40 wt. % isopropanol and 32 wt. % water), 1.5 to 2.5 wt. % peppermint oil, 0.5 to 1.5 wt. % zinc sulphate, 3 to 5 wt. % sodium hypochlorite, 2 to 5 wt. % camphor and otherwise water has proved to be particularly appropriate.

The material according to the invention is preferably produced in the manner described in U.S. Pat. No. 3,351,495 or DE-AS 1 495 123, in particular by extrusion and subsequent extraction (see also EP 0 425 784 B1). It is preferable here for the material according to the invention to be extruded in the form of a web, from which the desired shapes are then cut out. Spraying or coating with the solution of the antibacterial and fungicidal agents can be carried out after the extraction of the web or also after the desired shapes have been cut out of the web. The abovementioned publications are referred to in respect of the details of the extrusion, the extraction and the porosity which can be influenced by these.

The material to be used according to the invention has a pore size of less than 1 µm pore diameter, and in particular less than 0.5 µm pore diameter. Preferably, more than 50% of the pores have a diameter of 0.5 µm or less. Materials having an average pore size in the range from about 0.10 to 0.15 µm have proved to be particularly suitable. The void volume (porosity) is preferably at least 50%, and in particular at least 55%, for example 57 to 65%. However, it can also be up to 70 or even 80%.

When used as a shoe material, in particular as an inner sole, the web-like material preferably has ribs, at least on one side, which can be made of the same material as or a different material to the material to be used according to the invention. Ribs running parallel to one another at a distance of about 3 to 4 mm are preferred. However, ribs running in zigzag form or sinusoidal form are similarly particularly suitable. For use as an inner sole, these ribs should run at right angles to the longitudinal axis of the inner sole. In the case of ribs in zigzag form or sinusoidal form, in general 0.5 to 5 periods of the zigzag or wave form are present in the transverse direction to the longitudinal axis of the inner sole. The ribs not only improve the mechanical properties of the web-like material, but also lead to a good aeration, for example in the case of an inner sole between the inner sole and the base. By the interaction of the porosity of the material according to the invention used and the aerated hollow spaces formed by the ribs, a sponge effect is avoided, so that the bodily exhalations probably dry up substantially between the ribs. Furthermore, a layer of air forms as a result, leading to thermal insulation, so that the feet remain warm in the cold and cool under high heat.

In the case where the material to be used according to the invention is present in the form of a web, the thickness is about 0.025 to 1.5 mm, preferably about 0.2 to 1 mm, and in particular about 0.3 to 0.8 mm (e.g. about 0.5 mm). The height of the ribs depends on the thickness of the web of material, the desired use and the desired mechanical stability. When used as an inner sole, the total thickness of the material (web plus ribs) is usually about 2 mm.

It is obvious that the material to be used according to the invention can be used in all instances where sweat and other bodily exhalations are to be expected. Preferred fields of use are accordingly shoes, articles of clothing, underlays (for humans and animals), linings (for example for dog kennels and similar containers for keeping or transporting animals), inlays and parts thereof. The shape of the material to be used according to the invention can be adapted here to the particular intended use. For use in articles of clothing, for example, the shape of small pads which can be incorporated removably or replaceably into the articles of clothing is appropriate. For most intended uses, however, the web or sheet material described above, if appropriate with ribs on one or both sides, is preferred.

EXAMPLE

A web material was produced by extrusion and subsequent extraction as described in U.S. Pat. No. 3,351,495 and DE-AS 1 496 123. The resulting product comprised 51 vol. % silica, 40 vol. % ultra-high molecular weight polyethylene having an average molecular weight of $5.6 \times 10^6$, 2.5 vol. % carbon black (filler) and 0.5 vol. % antioxidant. The residual content of plasticizer (process oil) was 6 vol. %. By using suitable rolls, parallel ribs running at a distance of about 3 mm were produced on one side of the web-like material. The web-like material had a thickness of about 0.5 mm, while the ribs had a height of about 1.5 mm.

The average pore size of the product produced in this way was determined as 0.125 µm by mercury porosimetry. The void volume (porosity) was about 64%.

Inner soles were cut out of this web-like material and sprayed with a solution which had the abovementioned composition of surfactant, peppermint oil, zinc sulphate, sodium hypochlorite, camphor and water. About 5 g/m² of this solution were sprayed on.

The inner soles produced in this way were used by 30 persons over a relatively long period of time. All the persons unanimously reported that they observed no or at least a very greatly reduced formation of odour when wearing these inner soles.

What is claimed is:

1. A method of absorbing bodily exhalations, comprising contacting said exhalations with a material based on microporous, filler-containing polyolefin, which consists of a homogeneous mixture of 8 to 100 vol. % polyolefin having a weight average molecular weight of at least 300,000, a standard load melt index, measured in accordance with ASTM-D-1278-57T condition E, of substantially 0 and a reduced viscosity, measured with a solution of 0.02 g of the polyolefin in 100 g decalin at 130° C., of not less than 4.0, 1 to 92 vol. % finely divided silicon dioxide as filler and 1 to 40 vol. % plasticizer and has a pore size of less than 1 µm pore diameter.

2. The method according to claim 1, in which said material comprises 15 to 60 vol. % polyolefin, 35 to 80 vol. % filler and 1 to 10 vol. % plasticizer.

3. The method according to claim 1 or 2, in which the polyolefin is polyethylene.

4. The method according to claim 3, wherein said polyethylene is ultra-high molecular weight polyethylene.

5. The method according to claim 1 or 2, in which more than 50% of the pores of the material have a diameter of 0.5 µm or less.

6. The method according to claim 1 or 2, in which the void volume of the material is at least 50%.

7. The method according to claim 1 or 2, in which the plasticizer is process oil.

8. The method according to claim 1 or 2, in which the material is in the form of a web or sheet material or shapes cut from a web or sheet material.

9. The method according to claim 8, in which the web or sheet material has, at least on one side, ribs running parallel to one another.

10. The method according to claim 9, in which the material has been treated with antibacterial and/or fungicidal agents.

11. The method according to claim 1 or 2, in which the material has been treated with antibacterial and/or fungicidal agents.

12. The method according to claim 11, in which the material has been treated with a composition which consists of surfactant of tie formula R—O—$R_1$, in which R is a branched or straight-chain, substituted or unsubstituted alkyl, alkenyl or alkinyl radical having 6 to 50 carbon atoms and $R_1$ is an oxyalkyl, glyceroloxyalkyl or sorbitanoxyalkyl radical, peppermint oil, zinc sulphate, sodium hypochlorite, camphor, water and, optionally, a small amount of organic solvent.

13. A shoe having a sole, said sole comprising a microporous, filler-containing polyolefin, which consists of a homogeneous mixture of 8 to 100 vol. % polyolefin having a weight average molecular weight of at least 300,000, a standard load melt index, measured in accordance with ASTM-D-1278-57T condition E, of substantially 0 and a reduced viscosity, measured with a solution of 0.02 g of the polyolefin in 100 g decalin at 130° C., of not less than 4.0, 1 to 92 vol. % finely divided silicon dioxide as filler and 1 to 40 vol. % plasticizer and has a pore size of less than 1 $\mu$m pore diameter.

14. The shoe of claim 13, wherein said sole is an inner sole.

15. An article of clothing comprising a microporous, filler-containing polyolefin, which consists of a homogeneous mixture of 8 to 100 vol. % polyolefin having a weight average molecular weight of at least 300,000, a standard load melt index, measured in accordance with ASTM-D-1278-57T condition E, of substantially 0 and a reduced viscosity, measured with a solution of 0.02 g of the polyolefin in 100 g decalin at 130° C., of not less than 4.0, 1 to 92 vol. % finely divided silicon dioxide as filler and 1 to 40 vol. % plasticizer and has a pore size of less than 1 $\mu$m pore diameter.

* * * * *